United States Patent [19]

Batal et al.

[11] Patent Number: 5,047,163

[45] Date of Patent: Sep. 10, 1991

[54] ACTIVATION OF BLEACH PRECURSORS WITH SULFONIMINES

[75] Inventors: David J. Batal, Secaucus, N.J.; Stephen A. Madison, Valley Cottage, N.Y.

[73] Assignee: Lever Brothers Company, Division of Conopco, Inc., New York, N.Y.

[21] Appl. No.: 494,632

[22] Filed: Mar. 16, 1990

[51] Int. Cl.$^5$ .................. C11D 7/54; C11D 7/18; D06L 3/02

[52] U.S. Cl. ..................... 252/102; 8/110; 8/111; 252/99; 252/100; 252/173; 252/174; 252/174.12; 252/186.38; 252/186.43; 252/186.44; 252/545

[58] Field of Search .............. 252/102, 100, 94, 95, 252/99, 186.21, 186.44, 186.38, 186.43, 545

[56] References Cited

U.S. PATENT DOCUMENTS

| | | | |
|---|---|---|---|
| 2,809,937 | 10/1957 | Gray | 252/102 |
| 3,054,753 | 9/1962 | Hurt et al. | 252/102 |
| 3,153,565 | 10/1964 | Dithmar et al. | 252/102 |
| 3,183,266 | 5/1965 | Matzner | 252/102 |
| 3,245,913 | 4/1966 | Matzner | 252/102 |
| 3,948,795 | 4/1976 | Kawake et al. | 252/99 |
| 4,120,652 | 10/1978 | Scholer et al. | 252/97 |
| 4,123,376 | 10/1978 | Gray | 252/97 |
| 4,128,490 | 12/1978 | Finley et al. | 252/99 |
| 4,164,395 | 8/1979 | Finley et al. | 252/99 |
| 4,167,487 | 9/1979 | Gray | 252/102 |
| 4,169,805 | 10/1979 | Blumbergs et al. | 252/99 |
| 4,300,897 | 11/1981 | Gray | 252/97 |

OTHER PUBLICATIONS

"2-Arylsulphonyl-3-phenyloxaziridines: a New Class of Stable Oxaziridine Derivatives", Davis, Nadir and Kluger, J.C.S. Chem. Comm. 1977, p. 25.
"Synthesis of 2-Sulfonyl-and 2-Sulfamyloxaziridines Using Potassium Peroxymonosulfate (Oxone)", Davis, Chattopadhyay, Towson, Lal & Reddy, J. Org. Chem., 1988, vol. 53, p. 2087.
"Synthesis and Structure of 2-Arenesulfonyl-3-aryloxaziridines: a New Class of Oxaziridines"; Davis, Lamendola, Nadir, Kluger, Sedergran, Panunto, Billmers, Jenkins, Turchi, Watson, Chen and Kimura; J. Amer. Chem. Soc.; 1980, vol. 102, p. 2000.
"Selective Catalytic Oxidation of Sulfides to Sulfoxides Using N-sulfonyl-oxaziridines", Davis and Lal; J. Org. Chem. 1988, vol. 53, p. 5004.
Vishwakarma, L. C.; Stringer, O. D.; Davis, F. A. *Org. Synth.* 1987, 66, 203.
"Applications of Oxaziridines in Organic Synthesis" Davis, F. A; Sheppard, A. C. *Tetrahedron* 1989, 45, 5703.
"Chemistry of Oxaziridines. 2. Improved Synthesis of 2-Sulfonyloxaziridines" Davis, F. A.; Stringer, O. D. *J. Org. Chem.* 1982, 47, 1774.
"1,2-Benzisothiazole 1,1-Dioxides. Synthesis of 3-Alkyl-(or Aryl-) 1,2-benzisothiazole 1,1-Dioxides and Related Compounds", Abramovitch, R. A.; Smith, E. M.; Humber, M.; Purtschert, B.; Srinivasan, P. C.; Singer, G. M. *J. Chem. Soc. Perkin I* 1974, 2589.

*Primary Examiner*—Paul Lieberman
*Assistant Examiner*—A. Beadles-Hay
*Attorney, Agent, or Firm*—Milton L. Honig

[57] ABSTRACT

A bleaching composition is described that includes a peroxygen compound such as sodium perborate, an oxygen transfer agent such as a sulfonimine, and a bleach precursor such as TAED. These sulfonimines at relatively low concentrations enhance the activity of the precursor. A method for bleaching substrates is also provided, especially a method for cleaning fabrics.

38 Claims, No Drawings

ACTIVATION OF BLEACH PRECURSORS WITH SULFONIMINES

BACKGROUND OF THE INVENTION

1. Field of the Invention

The invention relates to a new type of low temperature bleaching system and a method for cleaning substrates therewith.

2. The Related Art

Many household and personal care products are formulated with an active oxygen-releasing material to effect removal of stain and soil. Oxygen-releasing materials have an important limitation; their activity is extremely temperature dependent. Temperatures in excess of 60° C. are normally required to achieve any bleach effectiveness in an aqueous wash system. Especially for cleaning fabrics, high temperature operation is both economically and practically disadvantageous.

The art has partially solved the aforementioned problem through the use of activators. These activators, also known as bleach precursors, often appear in the form of carboxylic acid esters or amides. In an aqueous liquor, anions of hydrogen peroxide react with the ester or amide to generate a corresponding peroxyacid which oxidizes the stained substrate. Commercial application of this technology is found in certain fabric bleaching detergent powders incorporating tetraacetylethylenediamine (TAED) and sodium nonanoyloxybenzene sulfonate (SNOBS).

TAED is effective only under warm-hot wash conditions, i.e. above 30° C. Although this material is widely employed in Europe with laundry detergent, cold water consumer washing habits have not permitted use in the United States. SNOBS can operate at lower temperatures than TAED. For this reason it has been commercialized in the United States but its performance could still be improved.

Another problem with carboxylic acid ester or amide bleach precursors such as TAED and SNOBS is that conversion to peracid is inefficient. A further difficulty is that they are not catalytic. Once the ester or amide has been perhydrolyzed it can no longer be recycled. Accordingly, relatively large amounts of precursor are necessary. Amounts as high as 8% may be necessary in a detergent formulation for bleaching fabrics. Cost for these relatively expensive chemicals is of major concern at such high use levels.

Outside the context of consumer products, there have been reports of catalytic oxidizing agents. F. A. Davis and coworkers, in a series of articles, reported preparation of a new class of stable oxidizing agents, namely 2-arenesulfonyl-3-aryl-oxaziridines. See Davis, Nadir, and Kluger, *J.C.S. Chem. Comm.* 1977, 25; Davis, Lamendola Jr., Nadir, Kluger, Sederjarn, Panunto, Billmers, Jenkins Jr., Turchi, Watson; Chen and Kimura, *J. Amer. Chem. Soc.* 1980, 102, 2000; and Davis, Chattopadhay, Towson, Lal and Reedy, *J. Org. Chem.* 1988, 53, 2087. These oxaziridines were prepared by peracid or monopersulfate oxidation of a corresponding sulfonimine under alkaline conditions. In late 1988, Davis published a paper entitled "Selective Catalytic Oxidation of Sulfides to Sulfoxides Using N-sulfonyloxaziridines", *J. Org. Chem.* 1988, 53, 5004. Therein described is a system where sulfonimine reacts with monopersulfate to generate an in situ oxaziridine in a toluene-water biphasic mixture. Oxaziridine then coverts the sulfide to a sulfoxide and generates starting sulfonimine, thereby rendering the process catalytic in nature. Beyond use as a synthetic tool, there is no suggestion of any possible application for sulfonimine chemistry to the problem of removing stain in consumer applications, such as in cleaning fabrics.

It is an object of the present invention to provide an improved bleaching system and detergent composition containing such system that operates over a wide temperature range including that of under 60° C.

It is another object of the present invention to improve the performance of bleach precursors that normally would be inoperative under low temperature wash conditions.

A further object of the present invention to provide bleach improvement through catalysts effective in relatively small amounts so as to avoid any substantial incremental costs.

A still further object of the present invention is to provide a method for bleaching stained substrates such as clothes, household hard surfaces including sinks, toilets and the like, and even dentures.

Other objects of the present invention will become apparent through the following summary, detailed discussion and examples.

SUMMARY OF THE INVENTION

A bleaching composition is provided comprising:

i) from about 1 to about 60% by weight of a peroxygen compound;

(ii) from about 0.05 to about 10% of an oxygen transfer agent whose structure is:

$$R^1R^2C=NSO_2R^3$$

wherein:

$R^1$ may be a substituted or unsubstituted radical selected from the grouping consisting of hydrogen, phenyl, aryl, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl, $R^1C=NSO_2R^3$, nitro, halo, cyano, alkoxy, keto, carboxylic and carboalkoxy radicals;

$R^3$ may be a substituted or unsubstituted radical selected from the group consisting of phenyl, aryl, heterocyclic ring, alkyl, cycloalkyl, nitro, halo, and cyano radicals;

$R^1$ with $R^2$ and $R^2$ with $R^3$ may respectively together form a cycloalkyl, heterocyclic, and aromatic ring system; and (iii) from about 0.1 to about 40% of a bleach precursor that reacts with peroxide anion and forms therewith a peracid, percarbonic acid or perimidic acid.

Additionally, there is provided a method for bleaching a stained substrate comprising treating the stained substrate with a peroxygen compound: an oxygen transfer agent whose structure is $R^1R^2C=NSO_2R^3$, with radical groups as defined above, and a bleach precursor.

DETAILED DESCRIPTION

Now it has been found that relatively small amounts of sulfonimines can boost the performance of bleach precursor-peroxygen compound systems. Increased effectiveness has been noted on consumer and industrial articles whose stains can be removed even at relatively low temperatures. Thus, sulfonimine chemistry is more than a synthetic curiosity as in the conversion of sulfides to sulfoxides reported by Davis et al. Unlike the Davis et al biphasic system that requires an organic solvent, sulfonimines can be devised for use in completely aqueous wash systems.

Sulfonimines covered by the present invention are those whose structure is:

$R^1R^2C=NSO_2R^3$ wherein:

$R^1$ may be a substituted or unsubstituted radical selected from the group consisting of hydrogen, phenyl, aryl, heterocyclic ring, alkyl, and cycloalkyl radicals;

$R^2$ may be a substituted or unsubstituted radical selected from the group consisting of hydrogen, phenyl, aryl, heterocyclic ring, alkyl, cycloalkyl, $R^1C=NSO_2R^3$ nitro, halo, cyano, alkoxy, keto, carboxylic and carboalkoxy radicals;

$R^3$ may be a substituted or unsubstituted radical selected from the group consisting of phenyl, aryl, heterocyclic ring, alkyl, cycloalkyl, nitro, halo, and cyano radicals; and $R^1$ with $R^2$ and $R^2$ with $R^3$ may respectively together form a cycloalkyl, heterocyclic or aromatic ring system.

Most advantageous are sulfonimines having at least one of $R^1$, $R^2$, $R^3$ substituted with a water-solubilizing functional group. These functional groups may be selected from carboxylates, phosphates, phosphonates, sulfates, sulfonates in acid or salt form. Suitable salts include those whose counterions are selected from alkali metal, ammonium, and $C_2$-$C_6$ alkanolammonium anions.

Amine functional groups may also be incorporated into $R^1$, $R^2$ or $R^3$ to provide water-solubilization of the sulfonimines. An example combining the amine and heterocyclic structure is that of pyridine.

A water-solubilizing functional group is one which renders the sulfonimines soluble to the extent of at least 2 mg/l, preferably at least 25 mg/l, optimally at least 250 mg/l in water at 25° C.

Heterocyclic rings according to this invention include cycloaliphatic and cycloaromatic type radicals incorporating an oxygen, sulfur and/or nitrogen atom within the ring system. Representative nitrogen heterocycles include pyridine, pyrrole, imidazole, triazole, tetrazole, morpholine, pyrrolidine, piperidine and piperazine. Suitable oxygen heterocycles include furan, tetrahydrofuran and dioxane. Sulfur heterocycles may include thiophene and tetrahydrothiophene. Among the various heterocycles, it has been found that those incorporating nitrogen are the most active.

The term "substituted" is defined in relation to $R^1$, $R^2$, $R^3$ as a substituent which is a nitro, halo, cyano, $C_1$-$C_{20}$ alkyl, amino, aminoalkyl, thioalkyl, sulfoalkyl, carboxyester, hydroxy, $C_1$-$C_{20}$ alkoxy, polyalkoxy and $C_1$-$C_{40}$ quaternary di- or trialkylammonium function.

Novel sulfonimine compounds are described below wherein $R^1$ is hydrogen, $R^2$ is phenyl with an X substituent, and $R^3$ is phenyl with a Y substituent. Very often X and Y groups are water-solubilizing groups, most commonly being carboxylic acid or salts thereof. Representative structures are as follows:

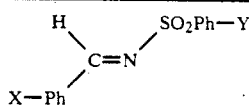

| | X | Y |
|---|---|---|
| SULF 1 | 4-$CO_2H$ | 4-Cl |
| SULF 2 | 4-$CO_2H$ | H |
| SULF 3 | 4-Cl | 4-$CO_2H$ |
| SULF 4 | H | 4-$CO_2H$ |
| SULF 5 | 4-$CO_2H$ | 4-$CO_2H$ |
| SULF 6 | 4-$CO_2H$ | 3-$NO_2$ |
| SULF 7 | 4-CN | 4-$CO_2H$ |
| SULF 8 | 4-OMe | 4-$CO_2H$ |
| SULF 9 | 3-OH | 4-Cl |

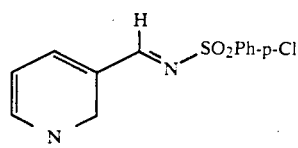

Illustrative of cycloaromatic and of heterocyclic nitrogen ring sulfonimines are the respective SULF 11 and SULF 12 whose structures are outlined below.

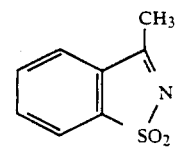

SULF 11

SULF 12

The following further compounds are illustrative of sulfonimines within the present invention.
N-Benzylidenebenzenesulfonamide
N-(4-Methylsulfinylbenzylidene)benzenesulfonamide
N-(4-Methylsulfonylbenzylidene)benzenesulfonamide
N-(3-Pyridinylmethylene)benzenesulfonamide
N-(4-Pyridinylmethylene)benzenesulfonamide
N-(2-Pyridinylmethylene)benzenesulfonamide
N-Benzylidene-3-pyridinesulfonamide
3-Trimethylammoniomethyl-1,2-benzisothiazole-1,1-dioxide chloride salt 1,2-Benzisothiazole-1,1-dioxide
N-(N-Methyl-3-pyridinylmethylene)benzenesulfonamide chloride salt
N-(4-Trimethylammoniobenzylidene)benzenesulfonamide chloride salt
N-Benzylidene-4-trimethylammoniobenzenesulfonamide chloride salt
N-(4-Cholyloxycarbonylbenzylidene)benzenesulfonamide chloride salt
N-Benzylidene-4-cholyloxycarbonylbenzenesulfonamide chloride salt
N-(4-Sulfoethylcarbonylbenzylidene)benzenesulfonamide sodium salt
Methyl N-(p-tolylsulfonyl)iminoacetate
Phenylsulfonyliminoacetic acid
N-(α-Methylbenzylidene)benzenesulfonamide
N-Isopropylidenebenzenesulfonamide
N-Benzylidenemethanesulfonamide
N-(4-Carboxybenzylidene)methanesulfonamide
N-Benzylidenetrifluoromethanesulfonamide N-(2,2,3,3,4,4,4-Heptafluorobutylidene)benzenesulfonamide
N-(4-Dimethylsulfoniumbenzylidene)benzenesulfonamide chloride salt
N-(2-Furfurylidene)-4-carboxybenzenesulfonamide
N-(2-Pyrrolylmethylene)benzenesulfonamide
N-(4-Phenoxycarbonylbenzylidene)benzenesulfonamide
N-(2,6-Dicarboxy-4-pyridinylmethylene)benzenesulfonamide disodium salt The foregoing oxygen transfer agents may be incorporated into detergent bleach compositions along with a further essential component which is a peroxygen compound capable of yielding peroxide anion in an aqueous solution.

Amounts of oxygen transfer agent suitable for the present invention may range from about 0.05 to 10%, preferably from about 0.2 to 5%, optimally between about 0.5% and 1.5% by weight of the composition.

The peroxygen compound may be present from about 1% to 65%, preferably from about 1.5% to 25%, optimally between about 2% and 10% by weight.

The molar ratio of peroxide anion (or a peroxygen compound generating the equivalent amount of peroxide anion) to oxygen transfer agent will range from about 1500:1 to about 1:2, preferably about 150:1 to about 1:1, optimally between about 60:1 to about 3:1.

Amounts of bleach precursor relative to oxygen transfer agent will be present in the molar ratio from about 250:1 to about 1:20, preferably from about 100:1 to about 1:1, optimally between about 25:1 to 2:1.

Peroxide anion sources are well known in the art. They include the alkali metal peroxides, organic peroxides such as urea peroxide, and inorganic persalts, such as the alkali metal perborates, percarbonates, perphosphates, persilicates and persulfates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions.

Alkylhydroperoxides are another suitable class of peroxygen compounds. Examples of these materials include cumene hydroperoxide and t-butyl hydroperoxide.

Organic peroxy acids may also be suitable as the peroxygen compound. Such materials have a general formula:

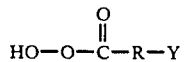

wherein R is an alkylene or substituted alkylene group containing from 1 to about 22 carbon atoms or a phenylene or substituted phenylene group, and Y is hydrogen, halogen, alkyl, aryl or

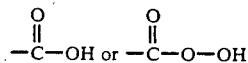

The organic peroxy acids usable in the present invention can contain either one or two peroxy groups and can be either aliphatic or aromatic. When the organic peroxy acid is aliphatic, the unsubstituted acid has the general formula:

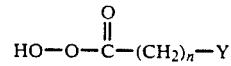

where Y can be, for example, H, $CH_3$, $CH_2Cl$, COOH, or COOOH; and n is an integer from 1 to 20.

When the organic peroxy acid is aromatic, the unsubstituted acid has the general formula:

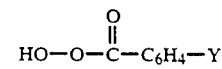

wherein Y is hydrogen, alkyl, alkylhalogen, halogen, or COOH or COOOH.

Typical monoperoxy acids useful herein include alkyl peroxy acids and aryl peroxy acids such as:
( i) peroxybenzoic acid and ring-substituted peroxybenzoic acids, e.g. peroxy-α-naphthoic acid;
( ii) aliphatic, substituted aliphatic and alkylaryl monoperoxy acids, e.g. peroxylauric acid, peroxystearic acid and N,N-phthaloylaminoperoxycaproic acid.

Typical diperoxy acids useful herein include alkyl diperoxy acids and aryldiperoxy acids, such as:
(iii) 1,12-diperoxydodecanedioic acid;
( iv) 1,9-diperoxyazelaic acid;
( v) diperoxybrassylic acid; diperoxysebacic acid and diperoxyisophthalic acid;
( vi) 2-decyldiperoxybutane-1,4-dioic acid;
(vii) 4,4'-sulfonylbisperoxybenzoic acid.

Particularly preferred organic acids are peracetic acid, monoperoxyphthalic acid (magnesium salt hexahydrate), and diperoxydodecanedioic acid. Under certain circumstances, hydrogen peroxide itself may directly be employed as the peroxygen compound.

A third critical element in the compositions of this invention is a bleach precursor that reacts with peroxide anion and forms therewith a peracid, percarbonic acid or perimidic acid. Precursors of this invention are water-soluble materials, being soluble generally to an extent of at least 1%, preferably at least about 5% by weight at 25° C. and pH 7. Certain precursors of this invention may further be defined by the Per-Acid Formation Test wherein the precursor will have a titre of at least 1.5 ml of 0.1 N sodium thiosulphate. This test may be found in U.S. Pat. No. 3,177,148 (Bright et al) herein incorporated by reference.

Precursors which may be utilized for purposes of the present invention include:

(a) N-diacylated and N,N'-polyacylated amines, such as N,N,N',N'-tetraacetyl methylene diamine and N,N,N',N'-tetraacetyl ethylene diamine, N,N-diacetylaniline, N,N-diacetyl-p-toluidine; 1,3-diacylated hydantoins such as, for example, 1,3-diacetyl-5, 5-dimethyl hydantoin and 1,3-dipropionyl hydantoin; acetoxy-(N,N,N')-polyacylmalonamide, for example acetoxy-(N,N')-diacetylmalonamide;

(b) N-alkyl-N-sulphonyl carbonamides, for example the compounds N-methyl-N-mesyl-acetamide, N-methyl-N-mesylbenzamide, N-methyl-N-mesyl-p-nitrobenzamide, and N-methyl-N-mesyl-p-methoxybenzamide;

(c) N-acylated cyclic hydrazides, acylated triazoles or urazoles, for example monoacetylmaleic acid hydrazide;

(d) O,N,N-trisubstituted hydroxylamines, such as O-benzoyl-N,N-succinyl hydroxylamine, O-acetyl-N,N-succinyl hydroxylamine, O-p-methoxybenzoyl- N,N-succinylhydroxylamine, O-p-nitrobenzoyl-N,N-succinylhydroxylamine and O,N,N-triacetyl hydroxylamine;

(e) N,N'-diacyl-sulphurylamides, for example N,N'-dimethyl-N,N'-diacetyl-sulphurylamide and N,N'-diethyl-N,N'-dipropionyl sulphurylamide;

(f) Triacylcyanurates, for example triacetyl cyanurate and tribenzoyl cyanurate;

(g) Carboxylic acid anhydrides, such as benzoic anhydride, m-chloro-benzoic anhydride, phthalic anhydride, 4-chloro phthalic anhydride;

(h) Esters, for example glycose pentaacetate, xylose tetraacetate, sodium acetyloxybenzene sulfonate, sodium nanoyloxybenzene sulfonate and sodium benzoyloxybenzenesulfonate;

(i) 1,3-Diacyl-4,5-diacyloxy-imidazolidine, for example 1,3-diformyl-4,5-diacetoxy-imidazolidine, 1,3-diacetyl-4,5-diacetoxy-imidazolidine, 1,3-diacetyl-4,5-dipropionyloxy-imidazoline;

(j) Tetraacetylglycoluril and tetrapropionyl-glycoluril;

(k) Diacylated 2,5-diketopiperazine, such as 1,4-diacetyl-2,5-diketopiperazine, 1,4-dipropionyl-2,5-diketopiperazine and 1,4-dipropionyl-3,6-dimethyl-2,5-diketopiperazine;

(l) Acylation products of propylenendiurea or 2,2-dimethylpropylenediurea (2,4,6,8-tetraaza-bicyclo-(3,3,1) -nonane-3,7-dione or its 9,9-dimethyl derivative), especially the tetraacetyl- or the tetrapropionyl-propylenediurea or their dimethyl derivatives;

(m) Carbonic acid esters, for example the sodium salts of p-(ethoxycarbonyloxy)-benzoic acid and p-(propoxycarbonyloxy)-benzenesulphonic acid;

(n) Acyloxy-(N,N')polyacyl malonamides, such as alpha-acetoxy(N,N')diacetyl malonamide; and (o) Quaternary ammonium substituted peroxycarbonic or carboxylic acid esters such as 2-(N,N,N-trimethylammonium) ethyl sodium 4-sulphophenyl carbonate.

The precursors mentioned under (a), (h) and (j) are of special interest, particularly N,N,N',N'-tetraacetyl-ethylene -diamine (TAED), tetraacetyl-glycoluril (TAGU), glucose pentaacetate, xylose tetraacetate, sodium acetyloxybenzene sulfonate (SABS) and sodium nonanoyloxybenzene sulfonate (SNOBS).

Bleach systems of the present invention may be employed for a wide variety of purposes, but are especially useful in the cleaning of laundry. When intended for such purpose, the peroxygen compound, oxygen transfer agent and precursor of the present invention will usually also be combined with surface-active materials, detergency builders and other known ingredients of laundry detergent formulations.

The surface-active material may be naturally derived, or synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 0.5 to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms.

Examples of suitable synthetic anionic detergent compounds are sodium and ammonium alkyl sulphates, especially those obtained by sulphating higher ($C_8$–$C_{18}$) alcohols produced for example from tallow or coconut oil; sodium and ammonium alkyl ($C_9$–$C_{20}$) benzene sulphonates, sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 15%, are used to give a beneficial effect on detergency. This is particularly valuable in compositions used in hard water when the soap acts as a supplementary builder.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and di- succinates, oxydisuccinate, crystalline or amorphous aluminosilicates and mixtures thereof.

Polycarboxylic homo- and co-polymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from about 1 to 80% by weight, preferably from 10 to 60% by weight.

Upon dispersal in a wash water, the initial amount of peroxygen compound should range anywhere from about 0.05 to about 250 ppm active oxygen per liter of water, preferably between about 1 to 50 ppm. Within the wash media the amount of oxygen transfer agent initially present should be from about 0.01 to about 300 ppm, preferably from about 5 to about 100 ppm. Bleach precursor may be present in the wash media in an amount from about 0.05 to 20 ppm, preferably from about 5 to about 100 ppm. Surfactant should be present in the wash water from about 0.05 to 1.0 grams per liter, preferably from 0.15 to 0.20 grams per liter. When present, the builder amount will range from about 0.1 to 3.0 grams per liter.

Apart from the components already mentioned, the detergent compositions of the invention can contain any of the conventional additives in the amounts in which such materials are normally employed in fabric washing detergent compositions. Examples of these additives include lather boosters such as alkanolamides, particularly the monoethanolamides derived from palmkernel fatty acids and coconut fatty acids, lather depressants such as alkyl phosphates and silicones, anti-redeposition agents such as sodium carboxymethylcellulose and alkyl or substituted alkylcellulose ethers, other stabilizers such as ethylene diamine tetraacetic acid and phosphonic acid derivatives (Dequest®), fabric softening agents, inorganic salts such as sodium sulphate, and, usually present in very small amounts, fluorescent agents, perfumes, enzymes such as proteases, cellulases, lipases and amylases, germicides and colorants.

The oxygen transfer agents in combination with a peroxygen compound may be useful for removing stains both in consumer type products and for industrial applications. Among consumer products incorporating this invention are laundry detergents, laundry bleaches, hard surface cleaners, toilet bowl cleaners, automatic dishwashing compositions and even denture cleaners. Stained consumer products benefiting from treatment with compositions of this invention may include clothes and other fabrics; household fixtures and appliances such as sinks, toilet bowls and oven ranges; tableware such as drinking glasses, dishes, cookware and utensils; and even dentures. Hair colorants may also be formulated with the bleach composition of this invention.

The bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in non-aqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Synthesis of N-Sulfonimines

Sulfonimines used for the present invention were prepared by a modified version of procedures set forth by Davis et al. Synthesis of the imines was accomplished by condensing commercially available aromatic aldehydes and sulfonamides. Thus, sulfonimines were prepared by heating equimolar amounts of the requisite sulfonamide and aldehyde in either toluene or chlorobenzene containing a catalytic amount of toluenesulfonic acid. Reaction vessels were either fitted with a drying tube (calcium sulfate) or with a nitrogen flow system. Any water formed from these condensations was removed by equipping the reaction vessels with a Soxhlet extractor containing 3A molecular sieves. Formation of product sulfonimines was monitored by TLC and $^1$H NMR analyses. Complete reaction times varied from 1.5 hours to 2 days. The carboxysulfonimine products were isolated by filtering the reaction mixtures at room temperature. Specific syntheses are outlined in the following examples which focus upon product yield and spectroscopic analyses.

N-Benzylidenebenzenesulfonamide was prepared by reacting an equimolar mixture of benzenesulfonamide and benzaldehyde diethyl acetal as described by Davis et al in *J. Amer. Chem Soc.* 1980, 102, 2000.

EXAMPLE 2

N-(4-Carboxybenzylidene)-4-chlorobenzenesulfonamide (SULF-1)

A well-stirred slurry consisting of 4.64g (31 mmol) of 4-carboxybenzaldehyde and 5.92 g (31 mmol) of 4-chlorobenzenesulfonamide and 20 mg of p-toluenesulfonic acid (TsOH) in 130 mL of toluene was heated to reflux for a total of 5 hours. The water formed from the reaction was removed by a Soxhlet extractor packed with 3A molecular sieves as described above. The mixture was allowed to cool to room temperature and was filtered to provide 9.76 g (98%) of SULF-1 as a white powder: mp >245° C.; IR (Nujol) 3300–2300 (br), 3090, 1689, 1616, 1168, 1013 cm$^{-1}$; $^1$H NMR (DSMO-d6, TMS ext standard, 60 MHz) δ9.15 (s, 1), 8.01 (s, 4), 7.79 (AB, 4, $J_{AB}$=11, $\Delta\nu$=16).

EXAMPLE 3

N-(4-Carboxybenzylidene)benzenesulfonamide (SULF-2)

In a manner similar to Example 2, 1.00 g (6.6 mmol) of 4-carboxybenzaldehyde, 1.05 g (6.6 mmol) of benzenesulfonamide and 20 mg of TsOH in 120 mL of toluene were heated for 2.5 hours to afford 1.82 g (90%)

of SULF-2 as a white powder; IR (Nujol) 3400–2400 (br), 1680, 1605, 1283, 1160, 1083 cm$^{-1}$; $^1$H NMR (DMSO-d6, TMS ext std)δ9 .17 (s, 1), 8.1–7.3 (m, 9).

EXAMPLE 4

N-(4-Chlorobenzylidene)-4-carboxybenzaldehyde (SULF-3)

In a similar manner to Example 2, 4.00 g (29 mmol) of 4-chlorobenzaldehyde, 5.72 g (29 mmol) of 4-carboxybenzenesulfonamide and 20 mg of TsOH in 150 mL of toluene were heated for 24 hours to provide 6.60 g (71%) of SULF-3 as a light tan powder: IR (Nujol) 3400–2500 (br), 1685, 1595, 1285, 1215, 1005 cm$^{-1}$; $^1$H NMR (DMSO-d6, TMS ext std)δ 9.15 (s, 1), 8.2–7.3 (m, 8).

EXAMPLE 5

N-Benzylidene-4-carboxybenzenesulfonamide (SULF-4)

In the same manner as Example 2, 4.00 g (38 mmol) of benzaldehyde, 7.58 g (38 mmol) of 4-carboxybenzenesulfonamide and 20 mg of TsOH in 150 mL of toluene were heated for 36 hours to afford 7.40 g (71%) of SULF-4 as a light tan powder: IR (Nujol) 3800–2600 (br), 1685, 1600, 1283, 1155 cm$^{-1}$; $^1$H NMR (DMSO-d6, TMS ext std)δ 9.05 (s, 1), 8.2–7.2 (m, 9).

EXAMPLE 6

N-(4-Carboxybenzylidene)-4-carboxvbenzenesulfonamide (SULF-5)

In the same manner as Example 2, 0.60 g (4 mmol) of 4-carboxybenzaldehyde, 0.80 g (4 mmol) of 4-carboxybenzenesulfonamide and 15 mg of TsOH in 80 mL of chlorobenzene under nitrogen were heated to provide 80% of SULF-5 as a light tan powder: IR (Nujol) 3400–2600 (br), 3082, 1688, 1614, 1160 cm$^{-1}$; $^1$H NMR (DMSO-d6, TMS ext std) δ9.17 (s, 1), 8.2–7.8 (m, 8).

EXAMPLE 7

N-(4-Carboxybenzylidene)-3-nitrobenzenesulfonamide (SULF-6)

In a similar manner to Example 2, 2.02 g (10 mmol) of 3-nitrobenzenesulfonamide, 1.50 g (10 mmol) of 4-carboxybenzaldehyde and 20 mg of TsOH in 150 mL of toluene were heated for 5 hours to yield 3.23 g (97%) of SULF-6 as a white powder: IR (Nujol) 3200–2500 (br), 1685, 1554, 1379, 1352, 1165 cm$^{-1}$; $^1$H NMR (DMSO-d6, TMS ext std)δ 9.24 (s, 1), 8.47 (s, 1), 7.9–6.9 (m, 7).

EXAMPLE 8

N-(4-Cyanobenzylidene)-4-carboxybenzenesulfonamide (SULF-7)

In a similar manner to Example 2, 1.25 g (9 mmol) of 4-cyanobenzaldehyde, 1.91 g (9 mmol) of 4-carboxybenzenesulfonamide and 20 mg of TsOH in 150 mL of chlorobenzene under nitrogen were heated for 18 hours to give 2.58 g (86%) of SULF-7 as a white powder: IR (Nujol) 3400–2400 (br), 2224, 1682, 1605, 1155 cm$^{-1}$; $^1$H NMR (DMSO-d6, TMS ext std)δ 9.35 (s, 1), 8.3–7.8 (m, 8).

EXAMPLE 9

N-(4-Methoxybenzylidene)-4-carboxybenzenesulfonamide (SULF-8)

In a similar manner to Example 2, 1.28 g (9 mmol) of anisaldehyde, 1.89 g (9 mmol) of 4-carboxybenzenesulfonamide and 20 mg of TsOH in 150 mL of chlorobenzene and under nitrogen were heated for 4.5 hours to yield 2.86 g (96%) of SULF-8 as a white powder: IR (Nujol) 3300–2700 (br), 1693, 1601, 1584, 1155 cm$^{-1}$; $^1$H NMR (DMSO-d6, TMS ext std)δ 8.91 (s, 1), 8.4–7.7 (m, 8), 3.92 (s, 3).

EXAMPLE 10

N-(3-Hydroxybenzylidene)-4-chlorobenzenesulfonamide (SULF-9)

In a similar manner to Example 2, 1.24 g (10 mmol) of 3-hydroxybenzaldehyde, 1.94 g (10 mmol) of 4-chlorobenzenesulfonamide and 20 mg of TsOH in 150 mL of toluene were heated for 12 hours to give 0.29 g (10%) of SULF-9 as a brown powder: IR (Nujol) 3400, 1658, 1556, 1458, 1155, 1025 cm$^{-1}$; $^1$H NMR (DMSO-d6, TMS ext std) δ8.85 (s,1), 8.73 (s, 1), 7.7–7.2 (m, 8).

EXAMPLE 11

N-terephthalidene-bis(4-carboxybenzenesulfonamide) (SULF-10)

In a similar manner to Example 2, 0.50 g (4 mmol) of terephthaldicarboxaldehyde, 1.50 g (8 mmol) of 4-carboxybenzenesulfonamide and 20 mg of TsOH in 100 mL of toluene were heated for 18 h to afford 90% of SULF-10 as a fine, light tan powder: IR (Nujol) 3400–2400 (br), 3081, 1689, 1597, 1154, 719 cm$^{-1}$; $^1$H NMR (DMSO-d6, TMS ext std) δ9.17 (s, 2), 8.3–7.8 (m, 12).

EXAMPLE 12

3-Methyl-1,2-benzisothiazole-1,1-dioxide (SULF-11)

This cyclic sulfonimine was prepared by reacting saccharin with 2 equivalents of methyllithium in tetrahydrofuran according to a procedure described in the *Journal of the Chemical Society. Perkin I*, 2589 (1974).

EXAMPLE 13

N-(3-Pyridinylmethylene)-4-chlorobenzenesulfonamide (SULF-12)

In a similar procedure to Example 2, 18.5 mmol of 3-pyridinecarboxaldehyde, 18.5 mmol of 4-chlorobenzenesulfonamide and 20 mg of TsOH in 100 mL of toluene reacted under reflux conditions to afford SULF-12 in 65% yield and high purity: $^1$H NMR (DSMO-d6, TMS ext std) δ9.3 (s,1), 9.2 (d, 1), 8.9 (m, 1), 8.4 (m, 1), 8.0–7.8 (AB. 4).

EXAMPLE 14

Activation of Peracid Precursor-Perborate Systems by Sulfonimines

Stain bleaching experiments were conducted in a Terg-O-Tometer in 500 mL of milli-Q water using two tea-stained cotton cloths measuring 3×4 inches. In a typical test, 0.75 g of Surf® added to the system and the pH of the solution was constantly buffered to the indicated level by the addition of dilute aqueous sodium hydroxide or hydrochloric acid. A given oxidant was added to the system followed by an appropriate amount of sulfonimine. Washes were carried out at 40° C. for 15 minutes.

Stain bleaching was measured reflectometrically using a Colorgard System/05 Reflectometer. Bleaching was indicated by an increase in reflectance, reported as ΔR. In general, a ΔR of one unit is perceivable in a paired comparison while a ΔR of two units is perceivable monadically.

The precursor TAED when formulated with sodium perborate monohydrate provides peracetic acid when placed in an alkaline aqueous medium. Table I reports results with TAED and various other peracid precursor-perborate systems both in the presence and absence of SULF-1.

When TAED ($9 \times 10^{-4}$ M) was used in conjunction with a large excess of sodium perborate, there was observed 4.1 units of bleaching on a tea-stained cloth. However, when a small amount of SULF-1 was included in the system, the overall bleaching performance improved to 12.4 units, representing an activation of over 200%.

Similarly, a comparable level of peracetic acid generated through the precursor sodium acetyloxybenzensulfonate (SABS) afforded a ΔR of 4.7 units, which was raised to 11.3 units of bleaching by addition of SULF-1. The perbenzoic acid precursor, sodium benzoyloxybenzenesulfonate (SBOBS) was also studied. At a low level (5 ppm), SBOBS delivered 2.3 units of bleaching at pH 9.5. When a stoichiometric amount of SULF-1 was included in the test, the overall bleaching became 3.8 units, demonstrating that SBOBS performance can be enhanced slightly by sulfonimines. The peracid precursor sodium nonanoyloxybenzenesulfonate (SNOBS) was also examined at pH 9.5 and 10.0. SNOBS provided 4.6 units of bleaching at pH 9.5 which could be increased to 5.1 upon the addition of a stoichiometric amount of SULF-1. When a similar experiment was conducted at pH 10, the performance of SNOBS dropped to 3.2, but still provided 5.1 units when accompanied by SULF-1.

TABLE I

Activations Using SULF-1

| Precursor | NaBO$_3$:Prec | pH | [SULF] × $10^{-4}$ M | [Prec] × $10^{-4}$ M | ΔR Prec | ΔR SULF |
|---|---|---|---|---|---|---|
| TAED | 12 | 9.5 | 6.0 | 9.0 | 4.1 | 12.4 |
| SABS | 3 | 10.1 | 3.0 | 18.6 | 4.7 | 11.3 |
| SBOBS | 5 | 9.5 | 3.0 | 3.0 | 2.3 | 3.8 |
| SNOBS | 5 | 9.5 | 3.0 | 3.0 | 4.6 | 5.1 |
| SNOBS | 5 | 10.0 | 3.0 | 3.0 | 3.2 | 5.1 |

The results set forth in Table I show that a variety of known peracid precursor - perborate bleaching systems can provide enhanced performance by the action of sulfonimines.

EXAMPLE 15

Effect of pH on the Activation of TAED By Sulfonimines

Bleaching performance of TAED in conjunction with sodium perborate exhibited variation of activity dependent upon pH conditions. At low pH, bleaching was maximized. At higher pH a reduction in performance was observed. Table II sets forth the data. These results were accumulated in a Terg-O-Tometer experiment using $9 \times 10^{-4}$M TAED with a 12:1 perborate ratio.

TABLE II pH Dependence on TAED Tea-stained Cloth Bleaching

| pH | 8.0 | 8.5 | 9.0 | 9.5 | 10.0 | 10.5 |
|---|---|---|---|---|---|---|
| ΔΔR | 6.2 | 5.7 | 4.7 | 4.1 | 4.0 | 2.5 |

Precursor SULF-1 through SULF-8 were tested in conjunction with TAED - perborate at varying pH levels between 8.0 and 10.5. Bleaching tests were conducted in a Terg-O-Tometer using two tea-stained cloths (3×4") in 500 mL of water containing 0.75 g of P-Surf®. TAED was dosed at $9 \times 10^{-4}$ M with a 12:1 sodium perborate monohydrate ratio. Sulfonimines were added at $6.0 \times 10^{-4}$ M concentration. Washes were performed at 40° C. for 15 min. Results of the pH profile on the TAED-SULF system are shown in Table III. The indicated ΔΔR values refer to the observed bleaching enhancement over the contribution from TAED alone, i.e.,

ΔΔR TAED-SULF=ΔR (TAED-SULF)−ΔR (TAED)

TABLE III

Dependence on TAED-Sulfonimine Tea-stained Cloth Bleaching ΔΔR TAED-SULF

| pH | SULF 1 | 2 | 3 | 4 | 5 | 6 | 7 | 8 | 9 | 10 | 12 |
|---|---|---|---|---|---|---|---|---|---|---|---|
| 10.5 | 4.8 | 5.3 | 7.0 | 5.1 | 1.1 | 6.1 | 10.4 | −0.4 | | | |
| 10.0 | 7.3 | 6.5 | 9.5 | 5.8 | 1.5 | 6.3 | 12.9 | 0.3 | 3.7 | | |
| 9.5 | 8.3 | 6.2 | 8.3 | 5.8 | 1.3 | 7.1 | 11.0 | 0.5 | | 9.1* | 12.4 |
| 9.0 | 6.6 | 4.5 | 7.9 | 4.2 | 0.5 | 7.4 | 11.3 | 0.2 | | | |
| 8.5 | 6.3 | 4.6 | 6.3 | 4.1 | 0.5 | 5.9 | 9.1 | 0.2 | | | |
| 8.0 | 5.6 | 2.6 | 2.4 | 3.3 | 0.0 | 3.9 | 8.8 | 3.5 | | | |

*Study conducted using $3 \times 10^{-4}$ M SULF.

From Table III, one can observe that for SULF 1-8, maximum bleaching enhancement takes place at pH 9.5 or 10.0. Comparing overall ΔR values (not shown) for the new bleaching system demonstrates that a high level of stain removal is accomplished at any point between pH 8.5 and 10.5. This feature of the TAED-SULF system is quite attractive since effective bleaching may result even when pH control is problematic.

Most of the sulfonimines provided significant activation of TAED. The sulfonimines which contain electron-withdrawing moieties (e.g. Cl, NO$_2$, or CN) provided maximum TAED enhancement. Conversely, those sulfonimines containing an electron-donating grouping, such as SULF-5 and SULF-8, provided minor bleaching enhancement. SULF-9 is the only activator shown which does not contain a carboxy group, but rather contains a hydroxyl. Although only studied at pH 10, notable cleaning enhancement was observed. SULF-10 is structurally distinctive because it contains two sulfonimine moieties. At one half the concentration of the other sulfonimines shown in Table III, an equivalent amount of bleaching occurred, suggesting that both imino groupings are utilized in the activation process.

SULF-7 provided the highest amount of TAED activation within the Table III series. Interestingly, SULF-7 also demonstrated slight activation (ΔΔR=2) of sodium perborate alone without TAED. It is believed that the cyano group is a major contributor to the high activity.

EXAMPLE 16

One of the most efficient oxygen transfer agents of this invention is SULF-11. Terg-O-Tometer cleaning tests with a SULF-11/TAED system were conducted on tea-stained cloth. The pH profile and concentration data are shown in Table IV. Even at such a low concentration as $1-5 \times 10^{-5}$ M SULF-11 there was achieved significant enhancement of TAED bleaching.

TABLE IV pH Dependence on TAED/SULF-11
Tea-stained Cloth Bleaching

| pH | ΔR TAED ($9 \times 10^{-4}$ M) | ΔR SULF-11/TAED ($6 \times 10^{-4}$ M) |
|---|---|---|
| 8 | 7.7 | 24.6 |
| 8.5 | 8.0 | 26.4 |
| 9 | 7.5 | 25.1 |
| 9.5 | 5.0 | 25.6 |
| 10 | 5.2 | 25.2 |
| 10.5 | 6.1 | 23.2 |

TABLE V

| Concentration TAED ($10^{-4}$ M) | Concentration SULF-11 | ΔR-TAED | ΔR-SULF |
|---|---|---|---|
| 9 | $6 \times 10^{-4}$ | 5.0 | 25.6 |
| 4.5 | $6 \times 10^{-4}$ | 3.0 | 20.5 |
| 9 | $3 \times 10^{-4}$ | 6.2 | 21.9 |
| 4.5 | $3 \times 10^{-4}$ | 3.9 | 19.5 |
| 9 | $1 \times 10^{-4}$ | 5.7 | 16.1 |
| 4.5 | $1 \times 10^{-4}$ | 4.4 | 13.9 |
| 4.5 | $5 \times 10^{-5}$ | 3.6 | 9.5 |
| 4.5 | $3 \times 10^{-5}$ | 4.1 | 8.2 |
| 4.5 | $1 \times 10^{-5}$ | 3.6 | 6.0 |

Conditions: pH 9.5; 15 min.; 40° C.; sodium perborate 6:1

EXAMPLE 17

Herein reported are the affects of varying concentration of sulfonimine, TAED and sodium perborate on tea-stain bleaching. These experiments were conducted under conditions similar to that of Example 15. Results are summarized in Table VI.

TABLE VI

Concentration Effects on TAED-SULF Tea-stain Bleaching

| SULF | [SULF] × $10^{-4}$ M | [TAED] × $10^{-4}$ M | NaBO$_3$:TAED | ΔR TAED | ΔR TAED-SULF |
|---|---|---|---|---|---|
| 1 | 6 | 9.0 | 12 | 5.6 | 13.7 |
|   |   | 4.5 | 12 | 2.4 | 7.5 |
|   | 3 | 9.0 | 12 | 5.7 | 12.1 |
|   |   | 4.5 | 12 | 2.4 | 6.9 |
|   | 1 | 9.0 | 12 | 6.1 | 9.6 |
|   |   | 4.5 | 12 | 2.6 | 5.0 |
| 6 | 6 | 9.0 | 12 | 6.2 | 14.5 |
|   |   | 9.0 | 6 | 5.9 | 12.8 |
|   | 3 | 9.0 | 12 | 5.9 | 10.5 |
|   |   | 4.5 | 12 | 2.7 | 7.9 |
|   | 1 | 9.0 | 12 | 5.2 | 9.1 |
|   |   | 4.5 | 12 | 2.6 | 4.9 |
| 2 | 6 | 9.0 | 12 | 3.2 | 9.4 |
|   | 3 | 9.0 | 12 | 3.7 | 8.1 |
|   |   | 4.5 | 12 | 1.9 | 5.9 |
| 4 | 6 | 9.0 | 12 | 3.8 | 9.6 |
|   | 3 | 9.0 | 12 | 5.6 | 9.5 |
|   |   | 4.5 | 12 | 3.6 | 6.7 |
| 3 | 6 | 9.0 | 12 | 3.4 | 11.7 |
|   | 3 | 9.0 | 12 | 4.6 | 10.4 |
|   |   | 4.5 | 12 | 3.4 | 9.7 |

Perhaps most noteworthy of all the data in Table VI are the entries which correspond to utilizing $1 \times 10^{-4}$ M sulfonimine. At this concentration, SULF 1 and 6 provided a doubling in performance relative to a low dosage ($4.5 \times 10^{-4}$ M) of TAED. The large enhancement obtained from this small amount of SULF material strongly supports the notion that the sulfonimines are behaving catalytically.

The TAED-SULF bleaching system as seen from the data operates efficiently at TAED concentrations between $4.5-9.0 \times 10^{-4}$ M and sulfonimine concentrations between $1 \times 10^{-5}$ M to $6 \times 10^{-4}$ M. The fact that such minute quantities of sulfonimines can enhance TAED performance is quite unusual and surprising.

EXAMPLE 18

Time Dependence on TAED-SULF Bleaching

A study was conducted to determine the effect of time on the TAED-SULF bleaching system. Table VII shows the data from an experiment conducted using tea-stained cloths in the Terg-O-Tometer with TAED and sodium perborate in the presence and absence of SULF-1. The amount of stain removal was measured in separate tests at 15, 30 and 45 minutes. The concentration of sulfonimine was varied between $3-6 \times 10^{-4}$ M with a constant $9.0 \times 10^{-4}$ M dosage of TAED. Not surprisingly, the bleaching by TAED alone increased gradually over a period of 45 minutes. More importantly, the bleaching performance by the sulfonimine containing system also escalated throughout the 45 minute period, regardless of SULF concentration. The net result after 45 minutes of washing is a doubling of TAED performance brought about by a relatively low level of sulfonimine.

TABLE VII

TAED - SULF-1 Bleaching Performance over Time

| [SULF-1] × $10^{-4}$ M | t min | ΔR TAED | ΔR SULF |
|---|---|---|---|
| 6 | 15 | 3.0 | 9.6 |
|   | 30 | 5.6 | 12.9 |
|   | 45 | 7.3 | 15.7 |
| 3 | 15 | 3.8 | 8.8 |
|   | 30 | 5.6 | 12.9 |
|   | 45 | 7.3 | 15.7 |

EXAMPLE 19

Variable Temperature Performance of the TAED-SULF Bleaching System

Bleaching results for the previous experiments were accumulated at a wash temperature of 40° C. Herein is demonstrated that the activation of TAED by sulfonimines also occurs at lower and higher wash temperatures. Experiments were conducted in a Terg-O-Tometer under conditions identical to those described earlier except that the wash temperature was kept at 12°-13° C. or 58°-59° C. SULF-1 was used as the oxygen transfer agent in these experiments at 6 or $3 \times 10^{-4}$ M with a $9.0 \times 10^{-4}$ M dosage of TAED. In the low temperature cases, activation of TAED by the sulfonimine was observed between 15 and 45 minutes, regardless of concentration. Analogously, the performance of TAED was enhanced at higher temperatures (about 60° C.) over a 30 minute washing period. It should be pointed out that these lower and higher temperatures represent the extremes found in actual fabric bleaching field conditions. The ability of sulfonimines to enhance TAED performance at variable temperatures may be of utility in countries where both hot and cold washes are practiced.

TABLE VIII

Effects of Temperature on TAED - SULF-1 Bleaching Performance

| [SULF-1] × $10^{-4}$ M | t min | Temp °C. | ΔR TAED | ΔR SULF |
|---|---|---|---|---|
| 6 | 15 | 12 | −0.2 | 1.8 |
|   | 30 | 13 | 1.3 | 4.1 |
|   | 45 | 13 | 1.7 | 5.5 |
| 3 | 15 | 12 | 0.0 | 1.2 |

TABLE VIII-continued
Effects of Temperature on TAED - SULF-1 Bleaching Performance

| [SULF-1] × $10^{-4}$ M | t min | Temp °C. | ΔR TAED | ΔR SULF |
|---|---|---|---|---|
|   | 30 | 13 | 1.2 | 3.7 |
|   | 45 | 12 | 2.1 | 5.3 |
| 6 | 15 | 58 | 7.3 | 11.1 |
|   | 30 | 59 | 12.3 | 14.6 |

EXAMPLE 20

Hydrophobic Stain Bleaching by Sulfonimines and TAED-Perborate Systems

A hydrophobic spaghetti stain was prepared by treating cotton cloths with spaghetti sauce. Removal of this stain was measured reflectometrically as described in Example 14. Bleaching of the oily stain is reported as ΔΔB, i.e. ΔΔB=(Reflectance of stained fabric washed with sulfonimine/TAED/perborate−reflectance of stained fabric before washing)−(reflectance of stained fabric washed with TAED/perborate alone−reflectance of stained fabric before washing).

The results using N-Benzylidenebenzenesulfonamide as oxygen transfer agent in conjunction with $4.5 \times 10^{-4}$ M TAED and 6:1 sodium perborate monohydrate in Surf ® at pH 9.5 and 40° C. (15 minute wash time) are shown in Table IX.

TABLE IX
Bleaching of Spaghetti Stain by Sulfonimine/TAED/Perborate Systems

| [SULF] × $10^{-4}$ M | ΔΔB |
|---|---|
| 1.0 | 2.0 |
| 0.5 | 1.0 |

The foregoing descriptions and Examples illustrate selected embodiments of the present invention. In light thereof, various modifications will be suggested to one skilled in the art all of which are within the spirit and purview of this invention.

What is claimed:

1. A bleaching composition comprising:
   (i) from about 1 to about 60% by weight of a peroxygen compound;
   (ii) from about 0.05 to about 10% of an oxygen transfer agent whose structure is:

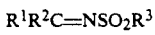
   $$R^1R^2C=NSO_2R^3$$

wherein:
   $R^1$ may be a substituted or unsubstituted radical selected from the grouping consisting of hydrogen, phenyl, aryl, heterocyclic ring, alkyl and cycloalkyl radicals;
   $R^2$ may be a substituted or unsubstituted radical selected from the group consisting of hydrogen, phenyl, aryl, heterocyclic ring, alkyl, cycloalkyl, $R^1C=NSO_2R^3$, nitro, halo, cyano, alkoxy, keto, carboxylic and carboalkoxy radicals;
   $R^3$ may be a substituted or unsubstituted radical selected from the group consisting of phenyl, aryl, heterocyclic ring, alkyl, cycloalkyl, nitro, halo, and cyano radicals;
   $R^1$ with $R^2$ and $R^2$ with $R^3$ may respectively together form a cycloalkyl, heterocyclic, and aromatic ring system; and
   (iii) from about 0.1 to about 40% of a bleach precursor that reacts with peroxide anion and forms therewith a peracid or perimidic acid.

2. A composition according to claim 1 wherein the peroxygen compound is present in an amount from about 1.5 to 25% and the oxygen transfer agent is present in an amount from about 0.2 to 5% by weight.

3. A composition according to claim 1 wherein the peroxygen compound is an inorganic material selected from the group consisting of perborate, percarbonate, perphosphate, persilicate and monopersulphate salts.

4. A composition according to claim 1 wherein at least one of $R^1$, $R^2$ and $R^3$ is substituted with a water-solubilizing functional group.

5. A composition according to claim 4 wherein the water-solubilizing functional group is selected from the group consisting of carboxylic acid, phosphoric acid, phosphonic acid, sulfuric acid, sulphonic acid and salts thereof.

6. A composition according to claim 1 wherein said substituent on $R^1$, $R^2$ and $R^3$ is a functional unit selected from the group consisting of nitro, halo, cyano, $C_1$-$C_{20}$ alkyl, amino, aminoalkyl, thioalkyl, sulfoxyalkyl, carboxyesters, hydroxy, $C_1$-$C_{20}$ alkoxy, polyalkoxy $C_1$-$C_{40}$ quaternary di- or tri-alkylammonium functional units and mixtures thereof.

7. A composition according to claim 6 wherein said quaternary alkylammonium functional unit is a cholyl group.

8. A composition according to claim 1 wherein the oxygen transfer agent is N-(4-carboxybenzylidene)-4-chlorobenzenesulfonamide.

9. A composition according to claim 1 wherein the oxygen transfer agent is N-(4-carboxybenzylidene)benzenesulfonamide.

10. A composition according to claim 1 wherein the oxygen transfer agent is N-(4-chlorobenzylidene)-4-carboxybenzenesulfonamide.

11. A composition according to claim 1 wherein the oxygen transfer agent is N-benzylidene-4-carboxybenzenesulfonamide.

12. A composition according to claim 1 wherein the oxygen transfer agent is N-(4-carboxybenzylidene)-4-carboxybenzenesulfonamide.

13. A composition according to claim 1 wherein the oxygen transfer agent is N-(4-carboxybenzylidene)-3-nitrobenzenesulfonamide.

14. A composition according to claim 1 wherein the oxygen transfer agent is N-(4-cyanobenzylidene)-4-carboxybenzenesulfonamide.

15. A composition according to claim 1 wherein the oxygen transfer agent is N-(4-methoxybenzylidene)-4-carboxybenzenesulfonamide.

16. A composition according to claim 1 wherein the oxygen transfer agent is N-(3-hydroxybenzylidene)-4-chlorobenzenesulfonamide.

17. A composition according to claim 1 wherein the oxygen transfer agent is N-terephthalidene-bis(4-carboxybenzenesulfonamide) (SULF-10) benzenesulfonamide.

18. A composition according to claim 1 wherein the oxygen transfer agent is 3-methyl-1,2-benzisothiazole-1,1-dioxide.

19. A composition according to claim 1 wherein the oxygen transfer agent is N-(3-pyridinylmethylene) benzenesulfonamide.

20. A composition according to claim 1 wherein the oxygen transfer agent is N-benzylidenebenzenesulfonamide.

21. A composition according to claim 1 wherein the oxygen transfer agent is 1,2-benzisothiazole-1,1-dioxide.

22. A composition according to claim 1 wherein the bleach precursor is N,N,N',N'-tetraacetylethylenediamine.

23. A composition according to claim 1 wherein the bleach precursor is tetraacetylglycoluril.

24. A composition according to claim 1 wherein the bleach precursor is glucose pentaacetate.

25. A composition according to claim 1 wherein the bleach precursor is xylose tetraacetate.

26. A composition according to claim 1 wherein the bleach precursor is selected from the group consisting of sodium nonanoyloxybenzenesulfonate, sodium benzoyloxybenzenesulfonate and sodium acetyloxybenzenesulfonate.

27. A composition according to claim 1 wherein the bleach precursor is present in an amount from about 1% to about 10% by weight.

28. A composition according to claim 1 further comprising about 1 to about 80% of a detergent builder.

29. A composition according to claim 1 further comprising an effective amount for cleaning of an enzyme selected from the group consisting of proteases, cellulases, lipases, amylases and mixtures thereof.

30. A composition according to claim 1 delivered in a form selected from the group consisting of a powder, sheet, pouch, tablet, aqueous liquid and non-aqueous liquid.

31. A method for bleaching a stained substrate, said method comprising contacting said stained substrate in an aqueous medium with a peroxygen compound, a bleach precursor and with an oxygen transfer agent whose structure is:

$$R^1R^2C=NSO_2R^3$$

wherein:
$R^1$ may be a substituted or unsubstituted radical selected from the group consisting of hydrogen, phenyl, aryl, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl, $R^1C=NSO_2R^3$, nitro, halo, cyano, alkoxy, keto, carboxylic and carboalkoxy radicals;

$R^3$ may be a substituted or unsubstituted radical selected from the group consisting of phenyl, aryl, heterocyclic ring, alkyl, cycloalkyl, nitro, halo, and cyano radicals;

$R^1$ with $R^2$ and $R^2$ with $R^3$ may respectively together form a cycloalkyl, heterocyclic, and aromatic ring system; and said peroxygen compound to oxygen transfer agent being present in a molar ratio ranging from about 1500:1 to about 1:2, and said bleach precursor to oxygen transfer agent being present in a molar ratio ranging from about 250:1 to about 1:20.

32. A method according to claim 31 wherein the ratio of peroxygen compound to oxygen transfer agent ranges from about 150:1 to about 1:1.

33. A method according to claim 31 where said substrate is a denture.

34. A method according to claim 31 wherein the ratio of bleach precursor to oxygen transfer agent ranges from about 100:1 to about 1:1.

35. A method according to claim 31 wherein the ratio of peroxygen compound to oxygen transfer agent ranges from about 60:1 to about 3:1 and the ratio of bleach precursor to oxygen transfer agent ranges from about 25:1 to about 2:1.

36. A method according to claim 31 wherein said substrate fabric.

37. A method according to claim 31 wherein said substrate selected from the group consisting of dishes, glassware and tableware.

38. A method for bleaching a stained substrate, said method comprising contacting said stained substrate in an aqueous medium with a peroxygen compound, a bleach precursor and with an oxygen transfer agent whose structure is:

$$R^1R^2C=NSO_2R^3$$

wherein:
$R^1$ may be a substituted or unsubstituted radical selected from the group consisting of hydrogen, phenyl, aryl, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl, $R^1C=NSO_2R^3$, nitro, halo, cyano, alkoxy, keto, carboxylic and carboalkoxy radicals;

$R^3$ may be a substituted or unsubstituted radical selected from the group consisting of phenyl, aryl, heterocyclic ring, alkyl, cycloalkyl, nitro, halo, an dcyano radicals;

$R^1$ with $R^2$ and $R^2$ with $R^3$ may respectively together form a cycloalkyl, heterocyclic, and aromatic ring system; and said contacting occurring in said medium containing about 0.05 to about 250 ppm active oxygen from the peroxygen compound, about 0.05 to about 200 ppm bleach precursor and about 0.01 to about 300 ppm oxygen transfer agent per liter of medium.

* * * * *